United States Patent [19]

Eliaz et al.

[11] Patent Number: 5,422,100
[45] Date of Patent: Jun. 6, 1995

[54] METHOD AND PRODUCT FOR TREATING SKIN AFFLICTIONS

[75] Inventors: Isaac G. Eliaz, 34 Ash Ave., San Anselmo, Calif. 94960; Shmuel Gonen, Kiryat-Ono, Israel

[73] Assignee: The Partnership Of Isaac G. Eliaz and Shruel Gonen, San Rafael, Calif.

[21] Appl. No.: 106,804

[22] Filed: Aug. 16, 1993

Related U.S. Application Data

[63] Continuation of Ser. No. 659,959, Feb. 25, 1991, abandoned, which is a continuation-in-part of Ser. No. 487,886, Mar. 2, 1990, abandoned.

[51] Int. Cl.$^6$ .................................................. A61K 7/06
[52] U.S. Cl. .................................. 424/70.11; 424/74; 424/78.02; 424/195.1; 424/70.1; 514/852; 514/861; 514/863; 514/864; 514/880; 514/881
[58] Field of Search ............. 424/70, 74, 78.02, 195.1; 514/852, 861, 863, 864, 880, 881

[56] References Cited

U.S. PATENT DOCUMENTS

| | | | |
|---|---|---|---|
| 3,939,260 | 2/1976 | Lafon | 424/401 |
| 4,048,301 | 9/1977 | Papantoniou | 424/70 |
| 4,460,488 | 7/1984 | Grollier et al. | 424/70 |
| 4,871,723 | 10/1989 | Makino et al. | 154/167 |
| 5,002,970 | 3/1991 | Eby, III | 424/440 |

OTHER PUBLICATIONS

The Merck Index, 10$^{th}$ ed., 1983, Merck and Co., Inc., Rahway, N.J. pp. 94,97,99,245 & 573.

*Primary Examiner*—Marianne M. Cintins
*Assistant Examiner*—M. Moezie
*Attorney, Agent, or Firm*—John A. Bucher

[57] ABSTRACT

Methods and products for promoting hair growth, preventing or minimizing hair loss, enhancing or restoring hair color or remelanization and treating other hair and skin afflictions are disclosed. The methods includes topical application of the products to the skin or hair follicles being treated. The product includes as an essential component a treatment agent in an amount effective for treating the affliction and selected from the class of chemicals consisting of anol, anethole, analogs of the above, polymers of the above and mixtures thereof. Various combinations of these chemicals may be found in herb families including umbelliferae, magnoliaceae, labiatae and rutaceae. The invention preferably contemplates selecting the treatment agent from the class of herbs consisting of *Foeniculum vulgares* (fennel seed), *Pimpinella anisum* (anise), *Carum carvi* (caraway seeds) and mixtures of the above herbs with each other and/or with other herbs.

10 Claims, No Drawings

METHOD AND PRODUCT FOR TREATING SKIN AFFLICTIONS

This is a continuation of application Ser. No. 07/659,959, filed on Feb. 25, 1991, now abandoned, which is a continuation-in-part of application Ser. No. 07/487,886, filed Mar. 2, 1990, now abandoned.

FIELD OF THE INVENTION

The present invention relates to methods and products for treating hair and skin conditions. In addition to hair treatments including promoting of hair growth, preventing, stopping or minimizing hair loss, conditioning the hair and scalp, thickening the hair, treating dandruff, etc. and treatments for skin conditions including smoothing of the skin, treating seborrheic dermatitis, treating psoriasis and treating like conditions, possibly including healing of wounds in the skin. The invention has also been found effective for restoring or enhancing hair color or remelanization.

BACKGROUND OF THE INVENTION

A wide variety of materials or compositions have been disclosed in the prior art as being effective for promoting hair growth and/or for preventing, stopping or minimizing hair loss as well as treating related conditions such as dandruff, itching of the scalp, etc.

A number of such treatment agents were disclosed in U.S. Pat. No. 4,874,791 issued Oct. 17, 1989 to Adachi, et al. In addition, that patent disclosed and claimed a hair-growing agent containing as an effective ingredient an aliphatic carboxylic acid having an odd number of carbon atoms or a derivative thereof.

U.S. Pat. No. 4,814,351 issued Mar. 21, 1989 to Mathews, et al. disclosed yet another scalp treatment for reducing average daily hair loss by periodically applying to the scalp a composition containing an active chelating agent. That reference was further of note in that its background statement set forth various theories for promoting hair growth.

U.S. Pat. No. 4,769,231 issued Sep. 6, 1988 to Ogura, et al. disclosed a hair tonic composition based upon the discovery that external or topical application of an extract from dong chong xia cao is capable of promoting hair growth.

U.S. Pat. No. 4,853,216 discussed the topical application of alpha$_1$ adrenergic agonist for producing a pilomotor effect to enhance shaving.

Still other references have dealt with various active agents for treating related conditions including various skin conditions. For example, U.S. Pat. No. 4,719,226 issued Jan. 12, 1988 to Otsuka, et al. disclosed a percutaneous absorption type preparation and process for preparing the product. U.S. Pat. No. 4,725,609 issued Feb. 16, 1988 to Kull, Jr., et al. disclosed the topical use of nicotinamide to promote angiogenesis, reepithelialization and wound healing. U.S. Pat. No. 4,656,192 referred to ester derivatives of tropolone as being useful antimicrobial agents, hair growth stimulants and dental medicines.

In addition to the above references, various herbs have long been known in Chinese herbology or medicine as having various medicinal or physiological applications. In particular, various herbs have been discussed as being effective for controlling the quality and color of hair as well as being effective hair growth agents.

In this connection, different herbs have been disclosed for treating premature graying of hair. These herbs include:

1. He shou wu—*Radix polygoni multiflori;*
2. Hei zhi ma—*Semen sesami indici;* and
3. Gou gi zi—*Fructus lycii* chinensis.

The above herbs were used particularly in oral applications such as in teas but were sometimes employed as local external or topical applications.

The following herbs have also been considered suitable for treating baldness in local or topical applications:

1. Gu sui bu—*Rhizoma gusuibu* (drynaria); and
2. Ce bai ye—*Cacumen biotae orientalis.*

Ce bai ye, according to Chinese literature, when made in a tincture from the fresh plant, has been tested and found to produce sprouting of hair on bald people, reportedly in at least thirteen cases. (Chinese Herbal Medicine, Materia Medica—Bensky Gamble, page 370.)

In any event, continuing efforts to discover or develop such materials demonstrates a continuing need for compositions or materials which are effective for promoting hair growth, preventing or minimizing hair loss and for treating various skin conditions. It is of course particularly important that such materials or compositions be uniformly effective and safe to use in order to enhance their effectiveness for use by large numbers of people.

SUMMARY OF THE INVENTION

Accordingly, there has been found to remain a need for improved methods and products for treating hair and skin conditions including promoting hair growth, preventing, stopping or minimizing hair loss, conditioning the hair and scalp, thickening the hair, treating dandruff, smoothing the skin, treating seborrheic dermatitis, treating psoriasis and treating like conditions, possibly including even the healing of wounds in the skin and like uses. Such a wide variety of applications is accordingly contemplated by the present invention and is to be understood as being intended by references to methods and/or products for treating hair and skin conditions.

The invention specifically contemplates the enhancement or restoration of hair color to its natural or "pre-gray" color or, in other words, remelanization of the hair. This may and usually has been found to result in a change in the hair color and enrichment of the hair color in addition to darkening the hair.

It is therefore an object of the invention to provide methods and products for treating such hair and skin conditions and also for color enhancement or restoration or remelanization of hair comprising topically applying to the skin or to the skin or scalp including hair and hair follicles of a host in need thereof a treatment composition containing as an essential component a treatment agent in a treatment effective amount and including an active ingredient selected from the class of chemicals consisting of anol, anethole, analogs of the above, polymers of the above and mixtures thereof.

Particular analogs include estragole which is allyl analog of anethole. Anol polymers include, for example, di-anol, known to have estrogenic-like activity. Dianethole and photoanethole are two polymers of anethole also having estrogenic-like activity.

Characteristics of such chemicals are discussed in a number of references, for example, an article entitled "Fennel and Anise as Estrogenic Agents" by Michael Albert-Puleo, published in *Journal of Ethnopharmacology*, 2 (1980) 337–344. Chemical structures of the above materials are set forth in that article which is accordingly incorporated herein as though set forth in its entirety.

For purposes of identification, referring again to the article noted immediately above, anol is commonly characterized as 4(1-propenyl)phenol; anethole is commonly characterized as p-propenyl anisol; and estragole, which is noted as an analog of anethole, is commonly characterized as methyl charicol-1-methoxy-4(2-propyl)benzene. The chemical, fenchone, discussed below for use in combination with the above chemicals, is commonly characterized as $C_{10}H_{16}O$.

Preferably, the invention contemplates mixtures of at least two or more of the above class of chemicals, in combination with each other and/or with fenchone, in the treatment composition. Such chemicals have been found to be particularly effective for synergistically enhancing treatment effectiveness and to facilitate penetration of the treatment composition into the skin, hair or hair follicles.

Some chemicals as listed above may be obtained from a variety of sources. For example, the chemicals and their polymers may be produced synthetically but preferably they are obtained from various herbs having effective amounts of one or more of the class of chemicals. Such herbs may be selected from the class of herb families consisting of umbelliferae, magnoliaceae, labiatae and rutaceae.

It is a further object of the invention to provide methods and products for treating hair and skin conditions wherein a treatment composition is topically applied to the skin and/or hair and hair follicles, the treatment agent including tinctures or extracts of one or more herbs selected from the class consisting of *Foeniculum vulgares* (fennel seed), *Pimpinella anisum* (anise), other types of anise, *Carum carvi* (caraway seeds) and mixtures thereof.

Although the present invention preferably contemplates topical application to the hair and/or skin to be treated, it is noted that such an application is generally believed necessary in order to provide an adequate concentration of the necessary chemicals in the local area of hair and/or skin to be treated. However, it is assumed that hair and/or skin treatment by such topical application may be enhanced or supplemented by additional internal consumption of the same herbs.

Preferably, the above herbs are employed in the treatment composition in various combinations with each other and/or with other herbs selected for synergistically enhancing treatment and/or delivery through the skin, hair or hair follicles.

Specifically, the present invention contemplates such methods and products wherein the treatment agent comprises a tincture or extract of *Foeniculum vulgares* (fennel seed). This single herb is believed to include the most effective combination of chemicals as discussed above for treating hair and skin conditions contemplated by the present invention.

The invention also specifically contemplates methods and products wherein the treatment agent comprises a tincture or extract of *Pimpinella anisum* (anise). This herb has also been found to provide a very effective combination of chemicals.

Both of the herbs discussed above, particularly fennel, are also preferably included in combination either with each other or with other herbs selected for synergistically enhancing treatment and/or delivery through the skin or hair follicles.

It is yet a further object of the invention to provide methods and products for treating hair and skin conditions including any of the combinations of chemicals and/or herbs noted above wherein the treatment composition further includes optional amounts of a carrier, a masking agent, a gelling agent, fragrances and preservatives as desired and a tincture solvent for the treatment agent.

Of the optional components noted above, the carrier provides a medium for the treatment agent and other components of the treatment composition as well as possible masking a strong smell possible for certain of the treatment agents. A typical carrier is gum mastic. The masking agent is also added for the purpose of masking strong smells as noted above and may preferably be formed from a tincture of one or more additional herbs. The gelling agent is of a type commonly employed in cosmetics and medicinal compositions for controlling the consistency or other physical characteristics of the treatment composition. The tincture solvent or a combination of different tincture solvents may be employed for forming the tinctures or extracts of the chemicals and/or herbs comprising the treatment agent. A number of solvents including alcohol, etc. may be used for preparing the tinctures.

In any event, the methods and products of the present invention have been found to be surprisingly effective in the treatment of hair and skin conditions as noted above and discussed in greater detail below.

Additional objects and advantages of the invention are made apparent in the following description and examples of the invention.

DESCRIPTION OF THE PREFERRED EMBODIMENTS

Methods and products for treating hair and skin conditions as summarized above are discussed in detail below. The methods and products are commonly based upon the inclusion of a treatment agent containing an active ingredient which is either selected from a class of chemicals of consisting of anol, anethole, analogs of the above, polymers of the above and mixtures thereof, either alone or in combination with each other and additional chemicals such as fenchone.

Of the above chemicals, fenchone alone is present in a Chinese herb, Ce bai ye, which has been known to be suitable for topical application to promote hair growth. It has also been known to employ that Chinese herb for treating other skin conditions such as minor burns. However, the effectiveness of that Chinese herb for treating such conditions was not previously known to be associated with its fenchone component. In addition, neither the above Chinese herb nor other hair growth agents have been found to produce the synergistic results novelly accomplished by combining the above class of chemicals either with each other or with additional chemicals such as fenchone.

Useful combinations of the above chemicals have also been found to be present in a selected class of herb families consisting of umbelliferae, magnoliaceae, labiatae and rutaceae.

The above herb families each include large numbers of herbs, only some of which have known uses. These herb families are discussed and outlined in a number of references. For example, the umbelliferae family is discussed at length in an article entitled "The Biology and Chemistry of the Umbelliferae" edited V. H. Heywood, Dept. of Botany, Univ. of Redding, England. Representative members of the above herb families are also set forth, for example, in a publication by Shui Ying Hu entitled *An Enumeration of Chinese Materia Medica* and published by Chinese University of Hong Kong 1980.

In any event, members of the above herb families are only of interest to the extent that they are suitable for human use. It is believed to be more important in connection with the theory of the present invention that the herbs be selected to include one or more of the chemicals discussed above.

Within the above herb families, treatment agents formed as tinctures or extracts of certain herbs particularly including *Foeniculum vulgares* (fennel seed) and also *Pimpinella anisum* (anise), *Carum carvi* (caraway seeds) and mixtures thereof have been found to be particularly effective in the present invention. Of those herbs, primarily *Foeniculum vulgares* and others such as *Pimpinella anisum* have been found to be most effective alone or preferably in combination with each other or with other herbs such as *Carum carvi*, et al. for synergistically enhancing treatment and/or delivery through the skin or hair follicles.

The discovery of the present invention was based at least in part upon the theory that chemicals and/or herbs containing those chemicals having local estrogenic-like effects capable of counteracting testosterone in the hair follicles would be particularly effective for promoting hair growth and/or for preventing, stopping or minimizing hair loss and/or for enhancing or restoring hair color or remelanization. That theory was based, at least partly, upon testosterone and like hormones being known causative factors for hair loss and/or male pattern baldness. It is further believed that the theory may also be extended to other hair and skin conditions as summarized above.

The above theory is set forth partly by way of explanation of the invention and partly to explain the contemplated advantages for the class of chemicals set forth above in treating hair and skin conditions and discussed herein. However, since the specific mechanism by which the chemicals and/or herbs of the present invention are effective for treating such hair and skin conditions is not precisely known, the above theory is not intended to be limiting in terms of the invention.

In connection with the theory set forth above, an extract or tincture of fennel seeds was first tested because that herb is known in western herbology for promoting lactation in mothers. At the same time, fennel seeds were found to contain all of the class of chemicals set forth above as well as fenchone in significant amounts. Anol and anethole in particular are major components of the volatile oil of fennel seeds. Similarly, anise includes anol and anethole but is much less active physiologically than fennel. This may be due to anise having a lower amount of certain other chemicals. Caraway seeds are also from the umbelliferae herb family and are also known to promote lactation. These three herbs, especially fennel seeds, have been found to be most effective either alone or in combination with each other and/or other herbs for synergistically enhancing treatment effectiveness and for facilitating penetration of the treatment composition into the skin, hair or hair follicles.

In any event, further details of the invention are set forth in the following examples and methods of use.

METHOD OF TREATMENT OR APPLICATION

Table 1 represents amounts of the four chemicals discussed above in a variety of different herbs. Thus, in accordance with the preceding description, Table 1 indicates a possible order of preference for certain herbs. In particular, note the heavy concentration of the first and second chemicals in the two preferred herbs, *Foeniculum vulgares* and *Pimpinella anisum*.

TABLE 1

|  | A<br>Anol | B<br>Anethole<br>(and polymers) | C<br>Fenchone | D<br>Estragole |
|---|---|---|---|---|
| (Labiatae)<br>*Herba agastache* | + | + |  | + |
| (Labiatae)<br>*Ocimum santtum* |  |  |  | + |
| (Labiatae)<br>*Ocimum basilicum* |  |  | — | + |
| (Rutaceae)<br>*Fagara schnifolia* |  |  |  | + |
| (Magnoliaceae)<br>*Magnolia kobus* | + | + |  | + |
| (Araceae)<br>*Acorus gamineus* |  |  |  | + |
| (Burseraceae)<br>*Boswellia serrata* |  |  |  | + |
| (Umbelliferae)<br>*Foeniculum vulgares* | +++ | +++ | + | + |
| (Umbelliferae)<br>*Pimpinella Anisum* | +++ | +++ |  |  |
| (Magnoliaceae)<br>*Illicium verum* | + | + |  |  |
| (Magnoliaceae)<br>*Illicium anisatum* | + | + |  |  |
| (Legumnosae)<br>*Wistaria floribunda* | + | + |  |  |
| (Cyprpssaceae)<br>Thuja (Biotae)<br>(Volatile oil of leaf) |  |  | + |  |
| (Magnoloaceae)<br>*Magnolia salicifolia* |  |  |  | + |

The methods and products of the present invention contemplate topical application of the treatment product to the skin or scalp, hair and hair follicles to be treated. Typically, about 2-3 cubic centimeters (cc), or very approximately about 2-3 grams, of the treatment product were applied to the skin or scalp in test treatments. However, smaller and larger amounts are also effective.

Furthermore, the treatment agent made up only a small portion of the treatment product during these tests. Generally, it is contemplated that the treatment agent in tincture form, may comprise as little as 0.5% or even as low as 0.2% by weight of the treatment product. More typically, the invention contemplates that the treatment agent in tincture form comprises in the range of about 1.2-50% by weight of the treatment composition, more preferably about 2-20% by weight of the treatment composition, and most preferably about 5-15% by weight, corresponding to actual tests conducted where the treatment agent in tincture form comprised about 7% by weight of the treatment product. However, the above concentrations are set forth only to define a preferred treatment product. It is again noted that a treatment product according to the present invention could include a very wide concentration range of the treatment agent in tincture form, depending upon concentration of the tincture and the specific therapeutic goal desired.

It is emphasized that the invention contemplates a very broad spectrum, as noted above, depending upon the concentration of the tincture in the final product. For example, the tincture or extract may preferably range from a ratio of 50 parts of solvent (IPM) to 1 part of ground fennel seed to a ratio of 1 part of solvent (IPM) to 2 parts of ground fennel seed. The solvent is of course not limited to IPM but may be other suitable solvents as well, as discussed elsewhere herein.

The concentration of the tincture in the final product may vary, for example, from 0.5 percent or as low as even 0.2 percent by weight, when using a more concentrated tincture, to almost 100 percent when using a more dilute tincture within the range mentioned.

Thus, the effective amounts of the active ingredients in the treatment agent are of course much smaller than the amount of the extract in the final product since only a small portion of the treatment agent in tincture form actually consists of the active ingredient. It is again noted that the active ingredients are selected from the class of chemicals consisting of anol, anethole, analogs of the above, polymers of the above and mixtures thereof. Fennel seed extract includes all of the above chemicals plus fenchone.

In summary, the effective amount of the active ingredients in the final product equals the amount of the active ingredients in the tincture/extract (in the preferred broad range specified for solvent:treatment agent (ground fennel seed) equaling 50 to 1:2) multiplied by the percentage of the tincture in the final product (0.2% to 100% as noted elsewhere). It is further noted that, if a chemical or chemicals forming the active ingredients of the treatment agent are synthesized or isolated and not part of a natural herbal extract, then the range of amounts and concentrations can be even broader than discussed above.

It is specifically to be noted that the present invention essentially requires topical (or external) application of the composition to the skin or hair of a host in need thereof. Such external treatment is contemplated for use by itself. In fact, tests conducted for the invention included only such external treatment. However, internal treatment may be used but only as a supplement to external or topical treatment as defined herein. Specifically, supplemental internal treatment is optional and not necessary to the invention while internal treatment by itself is not contemplated for the invention.

As for frequency of application, it is typically contemplated that the treatment product, in the form of either a hair cream or skin cream, or liquid or other form, for example, be applied from about twice a day to about twice a month to the skin area or scalp area being treated, and taken internally as well to possibly supplement or enhance external treatment. However, effective treatment is also possible with a frequency of application of, for example, from a maximum of three to four times daily or even more frequently to once a month or even less frequently.

Effective topical treatment appears to be from about once daily to once every three days with the applied composition remaining in place for at least about 15–30 minutes and preferably for a period of about 12–24 hours.

Particularly in terms of the method of treatment for the invention, it is noted that most tests conducted heretofore were in connection with promoting hair growth or preventing, stopping or minimizing hair loss while effects on enhancing color, or restoring gray hair to its original color or, in other words, remelanization, were also observed. This typically resulted in a change of hair color, darker hair color and enriched hair color. With the methods and products of the invention being employed for other purposed, particularly for treating various skin conditions, it is possible that different application amounts and rates may be desirable. In particular, it may be found that substantially different amounts, probably smaller quantities, may be desirable for treating certain skin conditions; however, it is again emphasized that the optimum amounts and frequencies of application are not specifically known for all applications.

EXAMPLE I

Method of Preparation for a Treatment Product Employed in Prior Testing

Principal testing was carried out with a treatment product including a treatment agent formed as a tincture of *Foeniculum vulgares* (fennel seed) in combination with a tincture of *Carum carvi* (caraway seeds). A preferred method for preparing that treatment product is described herein.

The primary herb, *Foeniculum vulgares*, was first ground into a powder and tinctured in isopropyl menristate (IPM), an organic solvent in a ratio of about one part of fennel seed powder to three parts of IPM solvent.

Vegetable gum, or gum mastic, (as a preferred carrier) was dispersed separately into IPM solvent in a ratio of about ten parts IPM solvent and one part gum mastic.

The fennel tincture was allowed to stand for about two weeks, mixing the tincture from time to time. After two weeks, the tincture was filtered to produce a clear liquid.

The clear fennel tincture was mixed in a blender with the dispersed mastic gum in a ratio of about nine parts fennel tincture and about one part gum mastic solution to produce a fennel tincture solution.

A second tincture was prepared by grinding *Carum carvi* (caraway seeds) into a powder which was then tinctured in isopropyl menristate (IPM) in a ratio of about one part caraway seeds and about nine parts of IPM solvent. This tincture was also allowed to stand for two weeks, with stirring. Thereafter, the caraway tincture was filtered to also produce a clear liquid.

The ratio of herb to solvent, for fennel and other herbs, can vary widely, for example, from 2:1 to as high as 1:50 or 1:75 or even 1:100.

About 3% by weight of the caraway tincture was then added to the clear fennel tincture solution to form a combined herb tincture solution.

About 1/2% by weight of a selected fragrance and about 1.5% by weight of a masking formula tincture, based on the clear fennel tincture, were then added to the combined herb tincture solution. The masking formula tincture was formed from eight different herbs used to produce a masking herb tincture in the same manner as described above for the fennel tincture and the caraway tincture. The eight herbs included in the masking formula tincture included *Herba drynariae, Fructus psoraleae, Polygoni multiflori, Herba agastache,* Thuja, Camomile, Mentha and Hibiscus.

The above components combined as described formed the basic active product for the treatment product of the invention. The basic active product was mixed with a gel in a ratio of about one part of basic active product and about twelve parts of gel. The gel consisted of one part of hydroxyethylcellulose and fifty parts of water with a preservative added as necessary or desired. However, any of a number of well known gels may be used with the invention.

Of the components noted immediately above, the fragrance and masking formula tincture were selected for producing a pleasing aroma in the basic active product while masking the harsher smell of certain components such as the volatile oils from the fennel seed. The gum mastic is used for two purposes. Initially, it also helps to mask the strong smell of the fennel volatile oils. In addition, the gum mastic serves as a good carrier with a capability for penetrating into the skin and/or hair follicles. The gel is used in a manner common for cosmetics and other medicinal preparations to control the consistency and other physical characteristics of the product. The gel is well known for such uses since it is hypoallergenic and is also easily absorbed by the skin.

Thus, the final concentration of components, with broad ranges in parentheses, in the resulting treatment product include:
1. Fennel tincture in IPM—7.5% (0.2 to nearly 100%)
2. Dispersed gum mastic in IPM—0.8% (0.02–10%)
3 Caraway tincture in IPM—0. 25% (0.025–30%)
4. Masking formula in IPM—0.15% (0.05–25%)
5. Fragrance—0.20% (can vary as necessary)
6. Preservative—0.1% (can vary as necessary)
7. Ultragel—as necessary (q.s 100%, balance)
Total—100% by weight Original tests as described below were carried out with ultragel as the gelling agent. However, the composition may also be formed with a synthetic high molecular weight cross-linked polymer of acrylic acid, more specifically an acrylate/$C_{10-30}$ alkyl acrylate copolymer available for example under the trade name CARBOMER 1342. Whereas the ultragel contained mostly water, the CARBOMER 1342 was used in a ratio of about 0.5–1.0 percent by weight with the remainder of the gelling agent being purified water.

In any event, the gelling agent is added as the last component of the composition in order to produce the preferred gel form for the composition.

Test results from a treatment product formed as described above are set forth below.

EXAMPLE II

Test Results

In over fifty males and females using the treatment product of the present invention as described above, with various stages of baldness, the following results were observed:
1. Hair loss was halted within 2-6 weeks. Nearly 100% of the participants who complained of prior hair loss reported that hair loss stopped.
2. After four months of treatment, in over 80% of the subjects, initiation of hair growth was observed. Even in those few who did not report hair growth but who continued the treatment, initiation of hair growth was observed after about six months. After one year of treatment in both males and females, in generally all states of baldness, new hair growth was observed in over ninety percent of the test subjects. These results were based upon tests with a group of about 100 men and women.
3. Female participants observed approximately 50–60% initiation of hair growth.
4. It was generally noted almost all participants in tests according to the present invention reported improvement in hair quality, thickness and health.
5. The participants also commonly reported a substantial decrease in dandruff. Similarly, those participants with seborrheic dermatitis also reported very significant improvement. Tests for psoriatic lesions in a few patients having those conditions also showed significant improvement. Excellent therapeutic results were noted from the treatment of the present invention in all scalp and skin ailments including but not limited to itching, dandruff, seborrheic dermatitis and psoriasis of the scalp.
6. Continued testing according to Example II and other examples of the present invention have indicated that use of the present invention, particularly in males over a period of about six months has achieved nearly a 100% response in reported hair growth and termination of hair loss.
7. During observation of results from tests as described above, a dramatic effect was also noted in the restoration of original hair color to gray or white hair. In this context, original hair color refers to the color of the hair before turning white. Accordingly, this effect of the invention is also referred to herein as remelanization of the hair. Thus, new hair growth and hair replaced as a part of the natural hair growth cycle according to the invention tended to restore melanin in the hair, or to achieve remelanization in the hair as noted above, so that those test subjects with graying hair were observed to have noticeably darkened hair, that is, hair approaching the original color before turning gray or an enhanced or changed color. This effect of color restoration or remelanization in the hair was observed in the vast majority of the test subjects with graying hair, nearly 100%.

EXAMPLE III

Further Test Procedures

More specific test procedures were carried out with thirty individuals, both male and female, ranging in age from about 23 to about 80. These test subjects employed the treatment product of the present invention prepared in accordance with Example I for periods of time ranging from as little as six days to as long as approximately six months.

The test subjects, at initiation of testing, had a variety of hair conditions ranging from substantially bald through receding hairlines to thinning hair and full heads of hair with varying degrees of hair falling out. Of approximately fifteen test subjects employing the treatment product of the invention for more than two months, only one test subject experienced no substantial change.

The other fourteen test subjects experienced varying degrees of success ranging from substantial new hair growth to hair loss being controlled at a normal rate for individuals with generally healthy heads of hair. Of the fifteen test subjects employing the treatment product of the invention for less than two months, six subjects experienced no change. Of those six subjects, three had employed the treatment product for less than two weeks. The remainder of the fifteen test subjects using the treatment product for less than two months also experienced varying degrees of success ranging from new hair growth to loss of hair being in a normal range.

In any event, the results of Examples II and III are believed to clearly demonstrate the efficacy and effectiveness of the treatment product of Example I.

EXAMPLE IV

Preparations of Other Treatment Products

Based upon theory, study of test results as set forth above and other factors, it is contemplated that a range of treatment products can be produced employing different active ingredients selected as noted above from the various chemicals and/or herbs to produce similar results as in Examples II and III. However, those results may not be as substantial in view of the preferred herb being employed in the treatment product of Example I. It is contemplated that the other herbs and/or chemicals of the present invention as described above will produce similarly effective treatment compositions.

EXAMPLE V

The various treatment products as generally discussed in Example IV are topically applied in the same manner noted above. In all of the examples, internal consumption may enhance treatment when combined with topical application. In particular, similar topical application is contemplated for various hair and skin conditions. In each such application, the treatment composition is topically applied to the area with the particular condition.

In Examples III–V, a dramatic result of the invention was observed in terms of substantial restoration of hair color to the hair color of the subject prior to the hair becoming gray or enhanced, changed or darker color or in other words, remelanization in the hair.

Thus, there have been described above various methods and products according to the present invention for treating various hair and skin conditions. Modifications in addition to those set forth specifically above are possible within the scope of the present invention which is thus defined only by the following appended claims, which are set forth as further examples of the invention.

What is claimed is:

1. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of anol, anethole, fenchone, polymers thereof and mixtures thereof; and an effective amount of at least one herb selected from the group consisting of umbelliferae, magnoliaceae, labiatae and rutaceae.

2. The method of claim 1 wherein the treatment composition contains one or more members selected from a carrier, a masking agent, a gelling, fragrances and preservatives as desired and a tincture solvent.

3. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of anol, anethole, fenchone, polymers thereof and mixtures thereof; and an effective amount of at least one herb selected from the group consisting of Foeniculum vulgares (fennel seed), Carum carvi (caraway seeds) and mixtures thereof.

4. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of anol, anethole, fenchone, polymers thereof and mixtures thereof; and an effective amount of at least one herb selected for enhancing treatment and/or delivery through the skin, hair or hair follicles.

5. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of anol, anethole, fenchone, polymers thereof and mixtures thereof; and an effective amount of a tincture or extract of Foeniculum vulgares (fennel seed).

6. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of anol, anethole, fenchone, polymers thereof and mixtures thereof; and an effective amount of a tincture or extract of anise.

7. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of Foeniculum vulgares (fennel seed), anise, Carum carvi (caraway seeds) and mixtures thereof; and an effective amount of at least one herb selected for enhancing treatment and/or delivery through the skin, hair or hair follicles.

8. The method of claim 7 wherein the treatment composition contains one or more members selected from a carrier, a masking agent, a gelling agent, fragrances and preservatives as desired and a tincture solvent.

9. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of Foeniculum vulgares (fennel seed), anise, Carum carvi (caraway seeds) and mixtures thereof; and an effective amount of a tincture or extract of Foeniculum vulgares (fennel seed).

10. A method for treating dandruff, conditioning the hair and/or scalp, treating seborrheic dermatitis, and/or treating psoriasis, comprising topically applying to a host in need thereof a treatment composition comprising an effective amount of at least one compound selected from the group consisting of Foeniculum vulgares (fennel seed), anise, Carum carvi (caraway seeds) and mixtures thereof; and an effective amount of a tincture or extract of anise.

* * * * *